United States Patent
Wang et al.

(10) Patent No.: US 10,760,120 B2
(45) Date of Patent: Sep. 1, 2020

(54) HIGH MULTIPLEX PCR WITH MOLECULAR BARCODING

(71) Applicant: QIAGEN SCIENCES, LLC, Germantown, MD (US)

(72) Inventors: Yexun Wang, Ellicott City, MD (US); Quan Peng, Germantown, MD (US)

(73) Assignee: QIAGEN SCIENCES, LLC, Germantown, MD (US)

( * ) Notice: Subject to any disclaimer, the term of this patent is extended or adjusted under 35 U.S.C. 154(b) by 323 days.

(21) Appl. No.: 15/544,764

(22) PCT Filed: Jan. 21, 2016

(86) PCT No.: PCT/US2016/014274
§ 371 (c)(1),
(2) Date: Jul. 19, 2017

(87) PCT Pub. No.: WO2016/118719
PCT Pub. Date: Jul. 28, 2016

(65) Prior Publication Data
US 2018/0002738 A1    Jan. 4, 2018

Related U.S. Application Data

(60) Provisional application No. 62/107,137, filed on Jan. 23, 2015.

(51) Int. Cl.
*C12Q 1/68* (2018.01)
*C12Q 1/686* (2018.01)
*C12Q 1/6869* (2018.01)

(52) U.S. Cl.
CPC ........... *C12Q 1/686* (2013.01); *C12Q 1/6869* (2013.01)

(58) Field of Classification Search
None
See application file for complete search history.

(56) References Cited

U.S. PATENT DOCUMENTS

| 8,795,961 B2 | 8/2014 | Rank et al. | |
| 2005/0069887 A1* | 3/2005 | Kitabayashi | C07K 14/195 435/6.12 |
| 2005/0170373 A1 | 8/2005 | Monforte | |
| 2006/0177867 A1* | 8/2006 | Evans | C12Q 1/6844 435/6.18 |
| 2010/0129874 A1* | 5/2010 | Mitra | C12P 19/34 435/91.2 |

FOREIGN PATENT DOCUMENTS

| WO | 2009/036525 A2 | 3/2009 | |
| WO | 2013/130512 A2 | 9/2013 | |
| WO | 2013/138510 A1 | 9/2013 | |
| WO | WO-2013138510 A1 * | 9/2013 | |
| WO | 2014/145992 A1 | 9/2014 | |
| WO | WO-2014145992 A1 * | 9/2014 | ......... C12N 15/1065 |
| WO | 2014/171898 A2 | 10/2014 | |

OTHER PUBLICATIONS

Qiagen GeneRead™ Size Selection Handbook, 24 pages, Dec. 2014.
Harismendy et al., "Evaluation of next generation sequencing platforms for population targeted sequencing studies," *Genome Biol.* 10(3): Article R32, 2009. (13 pages).
Kinde et al., "Detection and quantification of rare mutations with massively parallel sequencing," *PNAS* 108(23): 9530-9535, 2011.
McCloskey et al., "Encoding PCR Products with Batch-stamps and Barcodes," *Biochem. Genet.*: 2007, 6 pages.
Meynert et al., "Variant detection sensitivity and biases in whole genome and exome sequencing," *BMC Bioinformatics* 15(247): 2014, 11 pages.
Nguyen-Dumont et al., "A high-plex PCR approach for massively parallel sequencing," *BioTechniques* 55: 69-74, 2013.
Peng et al., "Reducing amplification artifacts in high multiplex amplicon sequencing by using molecular barcodes," *BMC Genomics* 16(589): 2015, 12 pages.
Shiroguchi et al., "Digital RNA sequencing minimizes sequence-dependent bias and amplification noise with optimized single-molecule barcodes,"*PNAS* 109(4): 1347-1352, 2012.

* cited by examiner

*Primary Examiner* — Tracy Vivlemore
*Assistant Examiner* — Sahana S Kaup
(74) *Attorney, Agent, or Firm* — Seed IP Law Group LLP

(57) ABSTRACT

The present disclosure provides methods and kits for performing high multiplex PCR using molecular barcodes. The methods disclosed herein separately extend a set of primers (BC primers) that each comprise a target-specific sequence, a molecular barcode and a universal sequence, and amplify the resulting extension products using another set of primers (LA primers) that each comprise another target-specific sequence and a universal sequence. The methods may further comprise amplification using universal primers (preferably comprising an adapter).

30 Claims, 8 Drawing Sheets

Specification includes a Sequence Listing.

| Uni.Primer1 | 5' AATGATACGGCGACCACCGAGATCTACACTCTTTCCCTACACGACGCTCTTCCGATCTAATGTACAGTATTGCGTTTG 3' |
|---|---|
| |                                           IlluminaAS1             US1 |
| Uni.Primer2 | 5' CAAGCAGAAGACGGCATACGAGATACATCGAGATCGGTGACTGGAGTTCAGACGTGTGCTCTTCCGATCTTTCTTAGCGTATTGGAGTCC 3' |
| |                              IlluminaAS2    IDX                                             US2 |

FIG. 6

HIGH MULTIPLEX PCR WITH MOLECULAR BARCODING

CROSS REFERENCE TO RELATED APPLICATION

This application claims the benefit under 35 U.S.C. § 119(e) to U.S. Provisional Application No. 62/107,137, filed Jan. 23, 2015, which application is hereby incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 830109_408_USPC_SEQUENCE_LISTING.txt. The text file is 2.0 KB, was created on Jul. 11, 2017, and is being submitted electronically via EFS-Web.

BACKGROUND

Technical Field

The present disclosure relates to methods and kits for performing high multiplex PCR with molecular barcodes.

Description of the Related Art

Over the last few years, next generation sequencing (NGS) has become a widely adopted technology in many aspects of discovery and translational research, especially in genomic DNA variant analysis and RNA expression analysis. The scope of these analyses can be either as wide as the whole genome and transcriptome, or as focused as specific regions and gene panels.

Targeted sequencing is particularly advantageous at achieving very high coverage of the region of interest while keeping the cost of sequencing and complexity of data interpretation under control. Having a very high sequencing coverage is especially important for discovering cancer mutations present at low fractions. For example, an average sequencing depth of >1000× is typically required for detecting single nucleotide variants (SNVs) present at 5% fraction with good confidence. To detect SNVs at less than 5% fraction, much higher sequencing depth is needed. In RNA analysis, targeted approach can provide more evidence of low expression transcripts, because in transcriptome sequencing, most sequence reads are consumed by mid and high abundant transcripts and often leave inadequate coverage of low abundant transcripts.

One of the most commonly used approaches to enrich a target region before NGS is PCR amplification directly from sample DNA using target specific primers. Although requiring more efforts in up front primer design and chemistry optimization, many people still employ PCR amplicon-based enrichment because in general, PCR process is easier to handle, has an overall shorter protocol, is more specific in terms of target sequence enrichment, and can easily accommodate much lower DNA input.

Existing target enrichment, library preparation and sequencing steps all utilize DNA polymerase and amplification process which will introduce substantial bias (non-uniform amplification) and artefacts (polymerase errors turning into sequence variants not present in the original samples). The PCR amplification bias will significantly affect quantification accuracy, as final sequence read counts may not accurately represent the relative abundance of original DNA and RNA fragments. Polymerase artefacts generated during the PCR cycles will most likely result in many "false" sequence variants present at low fractions in final sequence reads. These low level "false" variants will make it more difficult to distinguish real somatic mutations present at very low fraction (e.g., less than 2%) in the sample. The root cause of these problems is the inability to distinguish the sampling of different original molecules from the resampling of the same molecule by primers during the PCR process. Such problems are more exacerbated when more PCR cycles are needed in dealing with low input DNA or poor quality DNA.

To address above problems and improve the accuracy of NGS analysis, people have proposed the use of exogenous molecular barcodes (or molecular tags). The concept of molecular barcoding is that each original DNA or RNA molecule is attached to a unique sequence barcode. Sequence reads having different barcodes represent different original molecules, while sequence reads having the same barcode are results of PCR duplication from one original molecule. By employing molecular barcodes, polymerase artefacts generated during PCR can be distinguished from sequence variants present in original molecules. The target quantification can also be better achieved by counting the number of unique molecular barcodes in the reads rather than counting the number of total reads, as total read counts are more likely skewed for targets by non-uniform amplification.

Different variations of molecular barcodes have been applied in NGS applications. However, so far all reported cases have been related to the amplification of one or a few amplicons by primers containing molecular barcodes. As a result, those analyses have all been restricted to only very small regions.

SUMMARY

The present disclosure provides methods for amplifying target nucleic acids in a nucleic acid sample and kits useful in such methods as recited in the claims.

In one aspect, the present disclosure provides a method for amplifying target nucleic acids in a nucleic acid sample, comprising:

(a) extending each of a plurality of barcode primers (BC primers) to obtain extension products using the target nucleic acids as templates, wherein
  (i) each barcode primer comprises, from 5' to 3', a $1^{st}$ universal primer sequence (US1), a molecular tag sequence (MT), and a $1^{st}$ target-specific sequence (TS1),
  (ii) a plurality of barcode primers comprise at least 20 different barcode primers, and
  (iii) among the plurality of barcode primers (BC primers), the $1^{st}$ universal primer sequences (US1) are the same, but the $1^{st}$ target-specific sequences (TS1) are different;

(b) separating the plurality of barcode primers that have not been extended in step (a) from the extension products; and (c) amplifying the extension products of step (b) in the presence of a plurality of limited amplification primers (LA primers) to obtain a plurality of $1^{st}$ amplification products, wherein (i) each limited amplification primer comprises, from 5' to 3', a $2^{nd}$ universal primer sequence (US2) and a $2^{nd}$ target-specific sequence (TS2), and (ii) among the plurality of limited amplification primers, the $2^{nd}$ universal primer sequences (US2) are the same, but the $2^{nd}$ target-specific sequences (TS2) are different.

In a related aspect, the present disclosure provides a kit comprising:

(1) a plurality of barcode primers (BC primers), wherein (i) each barcode primer comprises, from 5' to 3', a $1^{st}$ universal primer sequence (US1), a molecular tag sequence (MT), and a $1^{st}$ target-specific sequence (TS1), (ii) a plurality of barcode primers comprise at least 20 different barcode primers, and (iii) among the plurality of barcode primers, the $1^{st}$ universal primer sequence (US1) are the same, the molecular tag sequences (MT) are different, and the $1^{st}$ target-specific sequence (TS1) are different; and (2) a plurality of limited amplification primers (LA primers), wherein (i) each limited amplification primer comprises, from 5' to 3', a $2^{nd}$ universal primer sequence (US2) and a $2^{nd}$ target-specific sequence (TS2), and (ii) among the plurality of limited amplification primers, the $2^{nd}$ universal primer sequences (US2) are the same, but the $2^{nd}$ target-specific sequence (TS2) are different.

BRIEF DESCRIPTION OF THE DRAWINGS

FIG. 6 shows the sequences of an exemplary pair of universal adapter primers, Uni.Primer1 (SEQ ID NO:7) and Uni.Primer2 (SEQ ID NO:8).

FIG. 10A show correlation between "measured" vs. "expected" numbers for each ERCC RNA transcripts represented by each amplicon. The x-axis represents log 2 values of known copies in the ERCC RNA spike-in mix. The y-axis represents log 2 values of average barcode or read counts for each amplicon (n=3). Both barcode count and read count from different sequencing runs were first normalized to a mean value of 10,000 for each run before being averaged. FIG. 10B show high reproducibility of the barcode assignment process. Three independent target enrichment experiments were performed. The x-axis represents the average barcode count for each amplicon. The y-axis represents CV for each amplicon calculated by either read counts or barcode counts. The upper right inset showed a magnified view of CVs for very low abundant amplicons.

DETAILED DESCRIPTION

Figure 1:
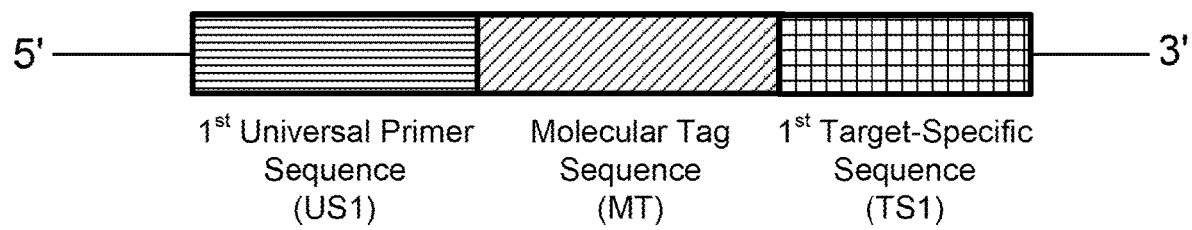
FIG. 1 is a schematic presentation of a barcode primer (BC primer).

PCR amplicon sequencing has been widely used as a targeted approach for both DNA and RNA sequence analysis. High multiplex PCR has further enabled the enrichment of hundreds of amplicons in one simple reaction. At the same time, the performance of PCR amplicon sequencing can be negatively affected by issues such as high duplicate reads, polymerase artifacts and PCR amplification bias. In recent times, there has been progress in addressing these shortcomings by incorporating molecular barcodes into PCR primer design. However, so far, most work has been demonstrated using one to a few pairs of primers, which limits the size of the region one can analyze at one time.

To apply molecular barcodes in high multiplex PCR, several technical hurdles must be overcome. For example, primer dimers present a very difficult problem for incorporating molecular barcodes into high multiplex PCR. This is because, to incorporate molecular barcodes to template nucleic acids, primers have to contain universal primer sequences at their 5' termini to allow subsequent amplification of the resulting barcoded template nucleic acids. Such universal primer sequences add a much higher risk of amplifying primer dimers during subsequent amplification ("universal amplification") using a primer pair that comprises the universal primer sequences. Many different primer dimers, each generated at a low level during the preparation of barcoded template nucleic acids, may be amplified together during the subsequent universal amplification to a level that severely hinders sequencing library preparation and sequencing analysis. In addition to primer dimers, another difficulty related to multiplex PCR is competition for amplification resource among many different amplicons resulting from their different amplification efficiency.

The present disclosure provides methods and kits that enable the use of molecular barcodes in high multiplex PCR, and can accommodate hundreds or more of target specific primers containing molecular barcodes in a single reaction. In addition, in preferred embodiments, the methods eliminate the need for ligation based library construction step, by adding sequencing adapters during multiplex PCR amplification. Such methods were successfully used in detecting SNVs at low fractions (e.g., 1%) (see Example 1 below), preparing a quality sequencing library using a small amount of sample DNA (see Example 2 below), and quantifying low abundant RNA transcripts with high reproducibility (see Example 3 below). These methods combine the simplicity of PCR amplicon sequencing with the accuracy of molecular barcodes, and are able to provide deep coverage for large regions. They also increase the specificity, sensitivity and reproducibility of various sequencing analysis, including variant calling and RNA transcript quantification.

The present methods use two sets of primers for preparing barcoded template nucleic acids. One set of primers, barcode primers (BC primers), comprise molecular tag sequences, while the other set of primers, limited amplification primers (LA primers), do not. To reduce primer dimers, in preferred embodiments, the BC primers and the LA primers are designed so that none of their 3' target-specific sequences contain more than a certain number of bases (e.g., 10 bases) that form perfect complementary matches with another primer.

In addition, to further reduce primer dimers and to reduce barcode resampling, the extension of the barcode primers using target nucleic acids as templates is carried out in a separate reaction from the subsequent amplification of the extension product using the LA primers. Specifically, the unused barcode primers (i.e., the barcode primers that have not been extended in the extension reaction) are separated from the extension products before the extension products are amplified in the presence of the LA primers. By separating the BC primers and LA primers into two reactions, the possibility of forming primer dimers between the BC primers and LA primers is minimized. Thus, even though barcoded template nucleic acids are not generated via traditional multiplex PCR per se where multiple target nucleic acids are amplified in the presence of multiple primer pairs specific to the target nucleic acids in a single reaction mixture, the present preparation of barcoded template nucleic acids nevertheless accomplishes the same results as using traditional high multiplex PCR, that is, generating multiple (e.g., hundreds or more) barcoded template nucleic acids in a single reaction vessel.

To further boost the targeted amplicons over undesirable primer dimes, in preferred embodiments, a universal primer comprising a universal primer sequence at the 3' termini of BC primers may be used together with the LA primers to form amplicons in limited PCR cycles. Such a step is also beneficial in minimizing competitions among target amplicons due to their different amplification efficiencies.

Additional approaches to facilitating the combination of molecular barcoding and high multiplex PCR and their advantages are also provided in detailed descriptions of the present methods and kits provided below.

In the following description, any ranges provided herein include all the values in the ranges. It should also be noted that the term "or" is generally employed in its sense including "and/or" (i.e., to mean either one, both, or any combination thereof of the alternatives) unless the content dictates otherwise. Also, as used in this specification and the appended claims, the singular forms "a," "an," and "the" include plural referents unless the content dictates otherwise. The terms "include," "have," "comprise" and their variants are used synonymously and to be construed as non-limiting. The term "about" refers to ±10% of a reference a value. For example, "about 50° C." refers to "50° C.±5° C." (i.e., 50° C.±10% of 50° C.).

In one aspect, the present disclosure provides a method for amplifying target nucleic acids in a nucleic acid sample, comprising: (a) extending each of a plurality of barcode primers (BC primers) to obtain extension products using the target nucleic acids as templates, (b) separating the plurality of barcode primers (BC primers) that have not been extended in step (a) (i.e., the "unused" barcode primers) from the extension products, and (c) amplifying the extension products of step (b) in the presence of a plurality of limited amplification primers (LA primers) to obtain a plurality of amplification products.

A nucleic acid sample that contains target nucleic acids to be amplified may be prepared from any samples that contain nucleic acids of interest. Exemplary include, but are not limited to, samples from a human, animal, plant, bacterium, or fungus, including blood, swabs, body fluid, liver, spleen, kidney, lung, intestine, brain, heart, muscle, pancreas, cell cultures, leaves, stems, flowers, roots, as well as lysates, extracts, or materials and fractions obtained from the samples described above, or any cells, microorganisms and viruses that may be present on or in the samples described above, and the like. A nucleic acid sample may also be prepared from processed samples including preserved, fixed and/or stabilized samples, such as formalin fixed and paraffin-embedded (FFPE samples) and other samples that were treated with cross-linking fixatives such as glutaraldehyde.

Nucleic acids may be isolated from a sample of interest to obtain a nucleic acid sample by any method known in the art useful for nucleic acid isolation or purification. In addition, many kits for nucleic acid preparation are commercially available and may be used, including QIAamp DNA mini kit, QIAamp FFPE Tissue kit, and PAXgene DNA kit.

Any nucleic acids of interest may be amplified according to the method provided herein. Nucleic acids particularly of interest are those known to be involved in diseases or disorders, including those mutations of which are associated with diseases or disorders or sensitivity or resistance to certain treatments. The diseases or disorders may be any diseases or disorders of interest, including but not limited to various types of cancers (e.g., human breast cancer, colon cancer, leukemia, liver cancer, lung cancer, ovarian cancer, prostate cancer, and gastric cancer), inherited disorders, neurological, metabolic, neuromuscular, developmental, cardiovascular, and autoimmune disorders.

Exemplary genes of interest include but are not limited to EGFR, BRAF, KRAS, ERBB2, PDGFRA, TP53, AKT1, ATM, FBXW7, PIK3CA, ALK, NRAS, BAX, TGFBR2, BRAC1, and BRAC2. Additional genes of interest include those disclosed in U.S. Patent Publication No. US 2013/0005613, which is incorporated by reference.

The number of different genes in target nucleic acids to be amplified may vary. Such a number may be between 5 and 1000, such as between 5 and 10, between 10 and 50, between 50 and 100, between 100 and 200, between 200 and 400, between 400 and 600, between 600 and 800, and between 800 and 1000. Preferably, the number of different genes to be amplified in a single multiplex PCR reaction is between 10 and 200, such as between 25 and 100.

In certain embodiments, the target nucleic acids are cDNA molecules, reverse transcribed from mRNAs of a sample of interest. In certain other embodiments, the target nucleic acids are microbial DNA molecules or mitochondrial DNA molecules. In some embodiments, the target nucleic acids are genomic DNA molecules.

Step (a) of the method provided herein is to assign different molecular barcodes to different target nucleic acids. In this step, a plurality of BC primers is extended using the target nucleic acids as templates. Each BC primer comprises, from 5' to 3', a $1^{st}$ universal primer sequence (US1), a molecular tag sequence (MT), and a $1^{st}$ target-specific sequence (TS1) (see FIG. 1). BC primers may be from 25 to 65 nucleotides, such as from 40 to 50 nucleotides in length.

A "primer" is an oligonucleotide that is complementary to a target nucleic acid and leads to addition of nucleotides to the 3' end of the primer in the presence of a DNA polymerase using the target nucleic acid as a template.

An "oligonucleotide" refers to a short polymer composed of deoxyribonucleotides, ribonucleotides or combinations thereof. Oligonucleotides are generally between about 10 to about 100 nucleotides, preferably about 12 to about 60 nucleotides, in length.

The $1^{st}$ universal primer sequence (US1) at the 5' terminus of a BC primer is a sequence that may be used for further PCR amplification. Preferably, this sequence does not have significant homology (i.e., US1 has less than 50% sequence identity over its full length) to target nucleic acids of interest or other nucleic acids in a nucleic acid sample. The US1 sequence may be from 11 to 35 nucleotides in length, such as from 15 to 25 nucleotides in length.

The molecular tag (MT) sequence in the middle portion of a BC primer is also referred to as barcode (BC) sequence. It is a sequence that will uniquely identify a particular target nucleic acid. The length of MT sequence may be from 3 to 20 nucleotides, such as from 5 to 15 nucleotides in length.

The MT sequence may be completely random, that is, any one of A, T, G, and C may be at any position of the MT sequence. Random barcodes are economical to synthesize. However, because they are completely random, they allow only limited ability to distinguish an original barcode from a "mutant" barcode due to PCR or sequencing errors. Those "mutant" barcodes decrease the ability to remove amplification artefacts in the reads.

One way to mitigate the above limitation is through barcode clustering, based on the assumption that any "mutant" barcode should come from an ancestor barcode with significantly higher number of reads. The possible number of different barcodes used in the methods provided therein is preferably significantly higher than the number of DNA molecules in a sample. Thus, the possibility for two DNA molecules receive the same or similar barcodes is low. If two barcodes are one edit distance away from each other, these two barcodes can be merged as one barcode cluster. In the end, the barcode cluster may be used in building consensus read and counting molecules. In practice, depending on the application, barcodes may be clustered and merged with different edit distances or stringency to obtain a desirable outcome.

In certain embodiments, the MT sequences are semi-defined or completely defined. Using such sequences can mitigate barcode errors. However, doing so, especially using completely defined MT sequences for many different primers in high multiplex PCR, may be cost prohibitive in some cases.

The $1^{st}$ target-specific (TS1) sequence at the 3' terminus of a BC primer is a sequence that specifically binds to a target nucleic acid, which allows the extension of the BC primer using the target nucleic acid as the template. The TS1 sequence is at least substantially and preferably completely complementary to a region of the target nucleic acid of interest.

The terms "complementary" and "complement" and their variants, as used herein, refer to any two nucleic acid sequences or portions thereof that form a hybridized duplex by base pairing. One nucleic acid fragment may be completely complementary to another nucleic acid fragment if all of the nucleotides in the fragment form base pairing with nucleotides in the corresponding antiparallel positions on the other nucleic acid fragment. "Partial" complementarity describes nucleic acid sequences in which at least 50%, but less than 100%, of the residues of one nucleic acid fragment are complementary to residues in the other nucleic acid fragment. A primer is "substantially complementary" to a target nucleic acid if at least 90% (e.g., at least 95%, at least 98%, or at least 99%) of the residues of the primer are complementary to residues in the target nucleic acid.

The TS1 sequence of a BC primer may be from 10 to 40 nucleotides, preferably from 15 to 25 nucleotides, in length.

As described above, in step (a), a plurality of BC primers are used to assign different barcodes to different target nucleic acids. Among the plurality of BC primers, the $1^{st}$ universal primer sequences (US1) are the same, but the $1^{st}$ target-specific sequences (TS1) are different. The same US1 sequence in different BC primers allows subsequent amplification of the extension products using a primer that comprises the US1 sequence at its 3' terminus.

To ensure that each copy of starting nucleic acids receives a unique MT sequence, the diversity of the MT sequences of each BC primer needs to be at least 10 fold (e.g., at least 15, 20, 25, 50 or 100 fold) higher than the original number of DNA copies in the input nucleic acid sample. Having a unique MT sequence links to every DNA copy allows the unique MT sequence to be used in counting and error correction during sequencing analysis.

To minimize primer dimers, each TS1 is selected to minimize potential cross hybridization with other primers, including other BC primers and LA primers. Preferably, a TS1 is redesigned when more than 8, 9, preferably 10, 11, or 12, bases at its 3' terminus form complete complementary matches with another primer.

An exemplary BC primer (with 10 bases complete random MT) is shown below:
5' AATGTACAGTATTGCGTTTTGNNNNNNNNNNCG-GCAGGAGACGAAGAG 3'
(SEQ ID NO:1) where AATGTACAGTATTGCGTTTTG (SEQ ID NO:2) at the 5' terminus of the BC primer is US1, and CGGCAGGAGACGAAGAG (SEQ ID NO:3) at the 3' terminus is TS1.

The number of different BC primers in step (a) is at least 20, preferably at least 50, at least 100, at least 300, at least 500, at least 750, or at least 1000. Such different BC primers in a single reaction allow analysis of a relatively large number of target nucleic acids, such as sequencing analysis that covers a large genomic region.

Figure 3:
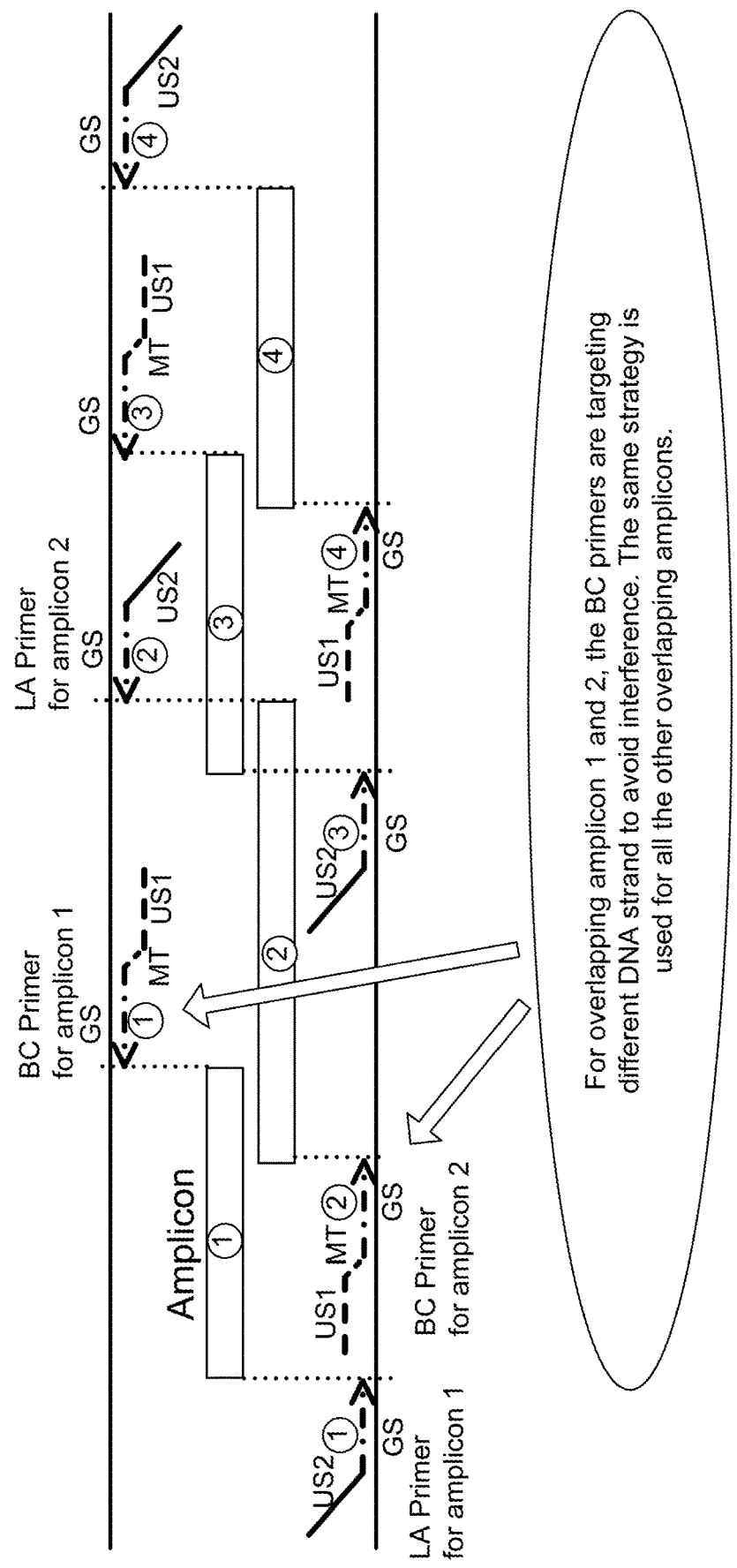
FIG. 3 shows a strategy for designing BC primers and LA primers for overlapping amplicons. "GS" refers to genomic target-binding sequence, "MT" refers to molecular tag sequence, and "US" in "US1" and "US2" refers to universal PCR primer binding sequence.

For an individual target nucleic acid or amplicon, whether the BC primer anneals to the plus or minus stand of DNA can be randomly selected. When there are two target nucleic acids or amplicons overlapping with each other in genomic DNA, the BC primers for each target nucleic acid or amplicon are selected in such a way that each BC primer will anneal to different strand of the DNA (see FIG. 3). This is to prevent the situation where polymerase extension of the upstream BC primer can displace downstream BC primer if two BC primers are positioned on the same strand in close proximity.

In general practice, to cover long continuous region with small amplicons suitable for NGS short reads, and leaving no uncovered region in between, amplicon overlapping is inevitable. In traditional multiplex PCR, overlapping amplicons are generally separated into different reaction pools (at least two pools required depending on the level of overlapping), otherwise closely located forward and reverse primers from overlapping amplicons will result in unintended smaller amplicons. The alternating strategy described herein combined with the other steps of the present methods enables single tube reactions even with overlapping amplicons.

Extension of BC primers may be performed by combining all BC primers, and target nucleic acids in a nucleic acid sample with a DNA polymerase in reaction buffer. Preferably, annealing to target nucleic acids by BC primers and/or extension of BC primers is performed at an elevated temperature, for example, at 50° C. to 75° C., such as at 55° C., 60° C., 65° C., 70° C. or 72° C., to increase the annealing specificity between target nucleic acids and BC primers. The target nucleic acids in the nucleic acid sample are typically first denatured, such as by incubated at a high temperature (e.g., 95° C. or 98° C.), before annealing with BC primers. Target nucleic acid denaturing, primer annealing, and primer extension may be performed in a thermal cycler. In certain embodiments wherein a hot-start DNA polymerase is used, DNA polymerase activation may also be simultaneously performed with target nucleic acid denaturing in a thermal cycler.

Preferably, DNA polymerases used for BC primer extension are thermostable. Exemplary DNA polymerases include Taq polymerase (from *Thermus aquaticus*), Tfi polymerase (from *Thermus filiformis*), Bst polymerase (from *Bacillus stearothermophilus*), Pfu polymerase (from *Pyrococcus furiosus*), Tth polymerase (from *Thermus thermophilus*), Pow polymerase (from *Pyrococcus woesei*), Tli polymerase (from *Thermococcus litoralis*), Ultima polymerase (from *Thermotoga maritima*), KOD polymerase (from *Thermococcus kodakaraensis*), Pol I and II polymerases (from *Pyrococcus abyssi*) and Pab (from *Pyrococcus abyssi*), Amplitaq Gold® DNA polymerase (Applied Biosciences), Stoffel fragment of Amplitaq® DNA Polymerase (Roche), KOD polymerase (EMD Biosciences), KOD Hot Start polymerase (EMD Biosciences), Deep Vent™ DNA polymerase (New England Biolabs), Phusion polymerase (New England Biolabs), Klentaq1 polymerase (DNA Polymerase Technology, Inc), Klentaq Long Accuracy polymerase (DNA Polymerase Technology, Inc), Omni KlenTaq™ DNA polymerase (DNA Polymerase Technology, Inc), Omni KlenTaq™ LA DNA polymerase (DNA Polymerase Technology, Inc), Platinum® Taq DNA Polymerase (Invitrogen), Hemo Klentag™ (New England Biolabs), Platinum® Taq DNA Polymerase High Fidelity (Invitrogen), Platinum® Pfx (Invitrogen), Accuprime™ Pfx (Invitrogen), and Accuprime™ Taq DNA Polymerase High Fidelity (Invitrogen).

In embodiments where amplicon overlapping occurs, the DNA polymerase preferably does not have strand displacement activity, flap endonuclease or 5'→3' exonuclease activity, with which the polymerase may destroy downstream product formed by other BC primers. An example of such preferred DNA polymerases is hot-start KOD DNA polymerase.

BC primer extension is limited to just one cycle to strictly avoid "barcode resampling."

After the completion of step (a), step (b) is to separate unused BC primers (i.e., BC primers that have not been extended) from extension products. The removal of unused BC primers further minimizes the risk of primer dimers formed between such primers and LA primers. In addition, it also minimizes the risk of the "barcode resampling" problem, that is, the same DNA template being associated with multiple molecular barcodes. Such a problem would defeat the benefits of molecular barcoding.

Preferably, the method for carrying out step (b) should be able to not only highly efficiently remove unused BC primers and primer dimers if any formed during step (a), but also recover as many extended products as possible to minimize sample loss. Sample loss may reduce sensitivity of downstream analysis such as variant detection.

Step (b) may be performed by size selection purification. The extension products are bound to target nucleic acids and may be purified using either bead or silica column based size selection system, such as Agencourt AMPure XP system and GeneRead Size Selection system. If needed, two or more rounds of purification with such a system may be used.

After the completion of step (b), step (c) is to amplify the extension products of (b) in the presence of a plurality of limited amplification primers (LA primers) to obtain amplification products.

Figure 2:
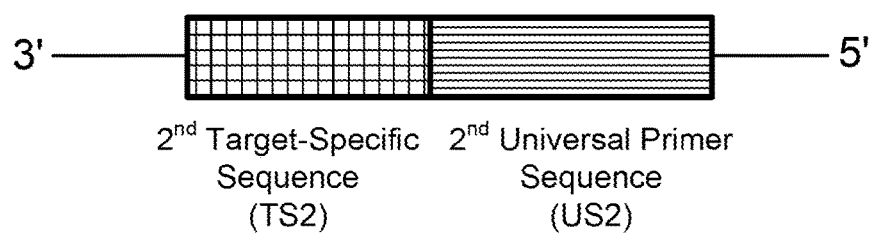
FIG. 2 is a schematic presentation of a limited amplification primer (LA primer).

Each LA primer comprises, from 5' to 3', a $2^{nd}$ universal primer sequence (US2) and a $2^{nd}$ target-specific sequence (TS2) (see FIG. 2). LA primers may be from 20 to 55 nucleotides, preferably from 30 to 45 nucleotides in length.

The $2^{nd}$ universal primer sequence (US2) at the 5' terminus of a LA primer is a sequence that may be used for further PCR amplification. Preferably, this sequence does not have significant homology (i.e., US2 has less than 50% sequence identity over its full length) to target nucleic acids of interest. The US2 sequence may be from 11 to 35 nucleotides in length, such as from 15 to 25 nucleotides in length.

The $2^{nd}$ target-specific (TS2) sequence at the 3' terminus of a LA primer is a sequence that specifically binds to the extension product of step (b), which allows the extension of the LA primer using the extension product as the template. The TS2 sequence is at least substantially and preferably completely complementary to a region of the target nucleic acid of interest incorporated into the extension product generated in step (a). The resulting extension product from the LA primer is a double-stranded DNA molecule that comprises US1 at 5' of one strand, US2 at 5' of the other strand, a MT sequence in the US1-containing strand, and a double-stranded region of the target nucleic acid delineated by TS1 and TS2. The TS2 sequence may be from 10 to 40 nucleotides, preferably from 15 to 25 nucleotides, in length.

As described above, in step (c), a plurality of LA primers are used to obtain amplification products that comprise barcoded target nucleic acids. Among the plurality of LA primers, the US2 sequences are the same, but the TS2 sequences are different.

To minimize primer dimers, each TS2 is selected to minimize potential cross hybridization with other primers, including BC primers and other LA primers. Preferably, a TS1 is redesigned when more than 8, 9, preferably 10, 11, or 12, bases at its 3' terminus form complete complementary matches with another primer.

An exemplary LA primer is shown below:

(SEQ ID NO: 4)
5' TTCTTAGCGTATTGGAGTCCAAAGCCGAGGAAGCTTTG 3' where TTCTTAGCGTATTGGAGTCC (SEQ ID NO:5) at the 5' terminus of the LA primer is US2, and AAAGCCGAGGAAGCTTTG (SEQ ID NO:6) at the 3' terminus is TS2.

The number of different LA primers in step (c) is at least 20, preferably at least 50, at least 100, at least 300, at least 500, at least 750, or at least 1000. Such different LA primers in a single reaction allow analysis of a relatively large number of target nucleic acids, such as sequencing analysis that covers a large genomic region.

In general, the number of different LA primers in step (c) is the same as that of different BC primers in step (a). Each LA primer pairs up with a BC primer to form a primer pair to amplify a region of a target nucleic acid delineated by the LA primer and the BC primer (see, e.g., FIG. 3).

A "primer pair" is a pair of primers, one of which is complementary to one strand of a target nucleic acid, and the other is complementary to the other strand of the target nucleic acid if the target nucleic acid is double-stranded or to a strand that is complementary to the target nucleic acid if the target nucleic acid is single-stranded. The extension of both primers amplifies the target nucleic acid or a portion thereof in a PCR reaction.

In certain embodiments, the number of different LA primers may be different from that of different BC primers. In certain embodiments, one LA primer may be paired to multiple BC primers.

Step (c) may be performed by combining all LA primers and the purified extension products from step (b) with a DNA polymerase in a PCR buffer. The DNA polymerase is the same as, or different from, the one used in step (a).

Although it is possible to carry out step (c) in the presence of only LA primers to perform linear amplification, preferably, another primer (referred to as "US1 primer") comprising the US1 sequence in the BC primers is also present in the amplification reaction via PCR. The PCR reaction is preferably done in limited cycles, such as 2 to 20 cycles, preferably 2, 3, 4, 5, 6, 7, 8, 9, 10, 11, 12, 13, 14, 15, or 16 cycles. The resulting amplicons have the MT sequence from the BC primers integrated with the US1 sequence at one end and the US2 sequence at the other end. Because the US1 primer is used, the PCR reaction is driven by LA primers at one end and common US1 primers at the other end. This strategy increases the enrichment efficiency, and more importantly out-compete primer dimers and nonspecific amplification. The limited number of cycles minimizes the difference in amplification efficiency and competition among many different amplicons.

The methods provided herein may further comprise step (d) that separate the unused LA primers (i.e., LA primers that have not been extended in step (c)) from the amplification products of step (c). This step may preferably also remove potential primer dimers. Step (d) may be performed using the same method as in step (b), such as via two rounds of Agencourt AMPure XP or GeneRead Size Selection purification.

The method provided herein may further comprise step (e) to further amplify barcoded template nucleic acids obtained in step (c) and optionally purified in step (d). The further amplification may be performed in the presence of a pair of universal primers, one of the universal primers comprises at its 3'-terminus the $1^{st}$ universal primer sequence (US1), and the other of the universal primers comprises at its 3'-terminus the $2^{nd}$ universal primer sequence (US2). The term "universal primer" used herein refers to a primer comprising the US1 or US2 sequence. The US1 primer described above in connection with step (c) is also a universal primer.

In certain preferred embodiments, each of the universal primers further comprises an adapter sequence located 5' to the universal sequence, US1 or US2. Such a universal primer is referred to as a "universal adapter primer." Sequencing platform specific adapter sequences are known in the art and may be included in universal adapter primers useful in performing step (e).

The amplification products obtained using the universal adapter primers have adapter sequences at both ends and thus together form a sequencing library. Such adapter sequences allow anchoring the DNA fragments of the sequencing library to a solid surface for high throughput sequencing via sequences complementary to the adapter sequence immobilized to the solid surface.

The adapter sequences in the two universal primers may be identical to each other, but preferably different from each other. The adapter sequences may be each about 10-100 nucleotides, such as about 12-60 nucleotides and about 15-50 nucleotides in length.

Figure 4:
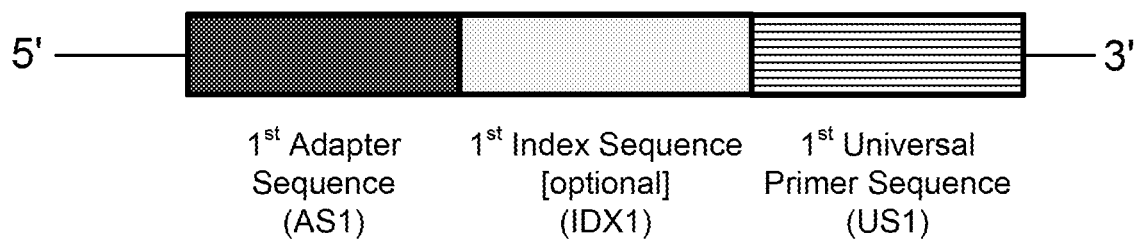
FIG. 4 is a schematic presentation of a universal adapter primer that comprises, from 5' to 3', a $1^{st}$ adapter sequence (AS1), an optional $1^{st}$ index sequence (IDX1), and a $1^{st}$ universal primer sequence (US1).
Figure 5:
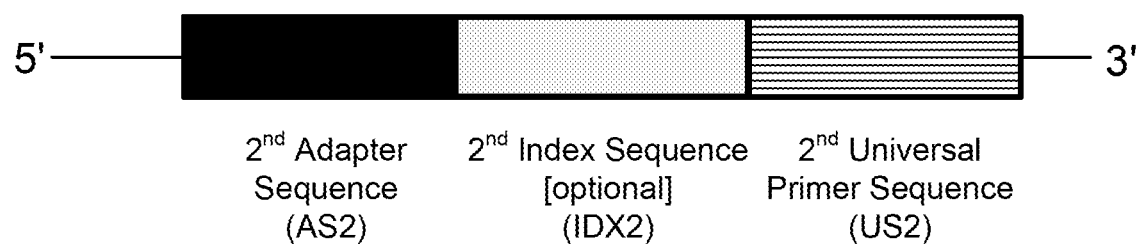
FIG. 5 is a schematic presentation of another universal adapter primer that comprises, from 5' to 3', a $2^{nd}$ adapter sequence (AS2), an optional $2^{nd}$ index sequence (IDX2), and a $2^{nd}$ universal primer sequence (US2).

In certain preferred embodiments, one or both of the universal adapter primers may comprise an index sequence (IDX) located between the adapter sequence and the universal primer sequence (see FIGS. 4 and 5). If both universal adapter primers each comprise an index sequence, the index sequences in these primers are different from each other.

An exemplary pair of universal adapter primers, Uni. Primer1 (SEQ ID NO:7) and Uni.Primer2 (SEQ ID NO:8) are shown in FIG. 6.

In certain other embodiments, the universal primers used in step (e) do not comprise any adapter sequence. Instead, a sequencing library is generated by ligating adapters to the amplification products of step (e).

The amplification products of step (e) may be directly used to ligate to one or more adapters. Alternatively, they may first be modified, such as by adding adenines to their 3' ends to facilitate ligation to one or more adapters having a T overhang.

Methods for ligating adapters to blunt-ended nucleic acids are known in the art and may be used in generating sequencing libraries from amplification products of PCR as provided herein. Exemplary methods include those described in Sambrook J and Russell D W, editors. (2001) Molecular Cloning: A Laboratory Manual. 3rd ed. Cold Spring Harbor, N.Y.: Cold Spring Harbor Laboratory, QIAGEN GENEREAD™ Library Prep (L) Handbook and U.S. Patent Application Publication Nos. 2010/0197509, 2013/0005613.

Similarly, methods for ligating adapters having a T overhang with modified amplification products having adenines added to their 3' ends are also known in the art (see, e.g., QIAGEN GENEREAD™ Library Prep (I) Handbook).

The adapters ligated to the two ends of a blunt-ended nucleic acid may be the same or different. Preferably, they are different. In certain embodiments, one of the two adapters may carry a group (e.g., a biotin group) to facilitate the isolation of adapted nucleic acids having two different adapters. For example, two adapters, "A" and "B," are ligated to the ends of nucleic acids. Adapter "B" carries a biotin group, which facilitates the purification of homoadapted nucleic acids (A/A or B/B). The biotin labeled sequencing library is captured on streptavidin beads. Nucleic acids containing the biotin labeled B adapter are bound to the streptavidin beads while homozygous, nonbiotinylated A/A adapters are washed away. The immobilized nucleic acids are denatured after which both strands of the B/B adapted nucleic acids remain immobilized by the streptavidin-biotin bond and single-strand template of the A/B nucleic acids are freed and used in sequencing.

In certain embodiments, the method disclosed herein may further comprise step (f) to sequence the amplification products from step (e). As described above, a sequencing library may be generated using universal adapter primers in step (e) or otherwise ligating adapter sequences to the amplification products from step (e).

The resulting sequencing library may be first amplified before being sequenced. Amplification of the sequencing library may be performed in situ, in emulsion or in solution, including bridge PCR and emulsion PCR. Alternatively, the sequence library may directly be sequenced without amplification.

Bridge PCR amplifies DNA fragments flanked with adapters (see, U.S. Pat. No. 5,641,658). A flat surface coated with two types of primers, corresponding to the adapters.

Amplification proceeds in cycles, with one end of each bridge tethered to the surface to form DNA colonies or DNA clusters.

Emulsion PCR isolates individual DNA molecules along with primer-coated beads in aqueous droplets within an oil phase (see, Williams et al., Nature Methods 3:545-50, 2006). A polymerase chain reaction then coats each bead with clonal copies of the DNA molecule.

Any high throughput sequencing platforms known in the art may be used to sequence the sequencing libraries prepared as described herein (see, Myllykangas et al., *Bioinformatics for High Throughput Sequencing*, Rodríguez-Ezpeleta et al. (eds.), Springer Science+Business Media, LLC, 2012, pages 11-25). Exemplary high throughput DNA sequencing systems include, but are not limited to, the GS FLX sequencing system originally developed by 454 Life Sciences and later acquired by Roche (Basel, Switzerland), Genome Analyzer developed by Solexa and later acquired by Illumina Inc. (San Diego, Calif.) (see, Bentley, Curr Opin Genet Dev 16:545-52, 2006; Bentley et al., Nature 456:53-59, 2008), the SOLiD sequence system by Life Technologies (Foster City, Calif.) (see, Smith et al., Nucleic Acid Res 38: e142, 2010; Valouev et al., Genome Res 18:1051-63, 2008), CGA developed by Complete Genomics and acquired by BGI (see, Drmanac et al., Science 327:78-81, 2010), PacBio RS sequencing technology developed by Pacific Biosciences (Menlo Park, Calif.) (see, Eid et al., Science 323: 133-8, 2009), and Ion Torrent developed by Life Technologies Corporation (see, U.S. Patent Application Publication Nos. 2009/0026082; 2010/0137143; and 2010/0282617).

In certain embodiments, step (f) is able to determine the sequence of an at least 10 kb, preferably at least 20 kb, 30 kb, 40 kb, 50 kb, 60 kb, 70 kb, 80 kb, 90 kb, 100 kb, 120 kb, or 150 kb region of DNA (e.g., genomic DNA) in a nucleic acid sample. The method disclosed herein allows generating sequencing data for a large region using a small input amount of nucleic acid sample. In some of such embodiments, the sequencing determination is accomplished using a nucleic acid sample containing about 0.1 ng to about 1 µg, such as about 0.1 ng to about 1 ng, about 1 ng to about 10 ng, about 10 ng to about 50 ng, about 50 ng to about 100 ng, about 100 ng to about 500 ng, and about 500 ng to about 1000 ng of genomic DNA (e.g., human genomic DNA).

The method disclosed herein may further comprise step (g) that determines the copy number of one or more target nucleic acid(s) in a nucleic acid sample. This step may use any method and software known in the art that allows such a determination based on sequencing data generated as described herein. Preferably, the copy number may be determined by counting unique molecular barcodes linked to the target nucleic acid(s).

The target nucleic acids are preferably cDNA molecules reverse transcribed from mRNAs isolated from mRNA-containing samples. Determining the copy number of one or more cDNA molecules in a nucleic acid sample may be used to determine the expression levels of the gene(s) that encode such mRNAs.

In certain embodiments, at least one of the target nucleic acids whose copy number is determined is of low abundancy in the nucleic acid sample. As used herein, a target nucleic acid is of low abundancy if the copy of the target nucleic acid is present in a nucleic acid sample at no more than 500 copies (e.g., no more than 400, 300, 200, 100, 50 or 10 copies). The method provided herein is especially useful in measuring low abundant target nucleic acids by calculating unique barcodes linked to the target nucleic acids (see Example 3).

The methods disclosed herein allow high technical reproducibility in measuring the copy number of one or more target nucleic acids. In certain embodiments, the coefficient of variation (CV) of the copy number determination of substantially all of the one or more target nucleic acids (i.e., at least 90% of the target nucleic acids measured) is less than 25%, preferably less than 20%, 15% or 10%.

The method disclosed herein may further comprise step (h) that identifies one or more genetic variations of interest in one or more target nucleic acids. This step may use any method and software known in the art that allows such identification based on sequencing data generated as described herein.

The use of barcodes in generating sequencing data helps removing sequencing artefacts and enables detecting genetic variations (e.g., SNVs) present in a nucleic acid sample at very low fractions. In certain embodiment, at least one genetic variation of interest has an allelic frequency of less than 5% in the nucleic acid sample. In certain other embodiments, at least one genetic variation of interest has an allelic frequency of less than 4%, 3%, 2%, or 1% in the nucleic acid sample. The low fraction mutations include those in heterogeneous samples, such as cancer samples.

In certain embodiments, the sensitivity of detecting at least one of the genetic variations of interest is at least about 60%, such as at least about 65%, 70%, 75%, 80%, or 85%. Sensitivity is the proportion of actual positives (i.e., the presence of a genetic variation of interest in a target nucleic acid) that are correctly identified as such. It can be expressed as (number of true positions)/(number of true positives+number of false negatives). Preferably, the sensitivity of detecting substantially all (i.e., at least about 75%, such as at least about 80% or 90%) of the genetic variations of interest is at least about 60%, such as at least about 65%, 70%, 75%, 80%, or 85%.

In certain embodiments, the specificity of detecting at least one of the genetic variations of interest is at least about 60%, such as at least about 65%, 70%, 75%, 80% or 85%. Specificity is the proportion of negatives (i.e., the absence of a genetic variation of interest in a target nucleic acid) that are correctly identified as such. It can be expressed as (number of true negatives)/(number of true negatives+number of false positives). Preferably, the specificity of detecting substantially all (i.e., at least about 75%, such as at least about 80% or 90%) of the genetic variations of interest is at least about 60%, such as at least about 65%, 70%, 75%, 80% or 85%.

In certain embodiments, both the sensitivity and specificity of detecting at least one of the genetic variations of interest is at least about 60%, such as at least about 65%, 70%, 75%, 80% or 85%. Preferably, both the sensitivity and specificity of detecting substantially all (i.e., at least about 75%, such as at least about 80% or 90%) of the genetic variations of interest is at least about 60%, such as at least about 65%, 70%, 75%, 80% or 85%.

In a preferred embodiment, the present disclosure provides a method for preparing a sequencing library, comprising:

(1) extending each of a plurality of barcode primers (BC primers) to obtain extension products using the target nucleic acids as templates, wherein (i) each barcode primer comprises, from 5' to 3', a $1^{st}$ universal primer sequence (US1), a molecular tag sequence (MT), and a $1^{st}$ target-specific sequence (TS1), (ii) a plurality of barcode primers comprise at least 50 (e.g., at least 100, 250, 500, 750, or 1000) different barcode primers, and (iii) among the plurality of barcode primers (BC primers), the $1^{st}$ universal primer sequences (US1) are the same, but the $1^{st}$ target-specific sequences (TS1) are different;

(2) separating the plurality of barcode primers that have not been extended in step (1) from the extension products;

(3) amplifying the extension products of step (b) in the presence of a primer that comprises the US1 sequence and a plurality of limited amplification primers (LA primers) to obtain a plurality of $1^{st}$ amplification products via a limited cycles (e.g., 2-16 cycles) of PCR, wherein (i) each limited amplification primer comprises, from 5' to 3', a $2^{nd}$ universal primer sequence (US2) and a $2^{nd}$ target-specific sequence (TS2), and (ii) among the plurality of limited amplification primers, the $2^{nd}$ universal primer sequences (US2) are the same, but the $2^{nd}$ target-specific sequences (TS2) are different, (4) separating the plurality of limited amplification (LA) primers that have not been extended in step (3) from the $1^{st}$ amplification products; and (5) amplifying the $1^{st}$ amplification products in the presence of a pair of universal adapter primer to obtain a sequencing library, wherein the $1^{st}$ universal adapter primer comprises, from 5' to 3', a $1^{st}$ adapter sequence and the US1 sequence, and the $2^{nd}$ universal adapter primer comprises, from 5' to 3', a $2^{nd}$ adapter sequence and the US2 sequence.

The method may optionally comprise step (6) to separate the universal adapter primers from the sequencing library.

Figure 7:
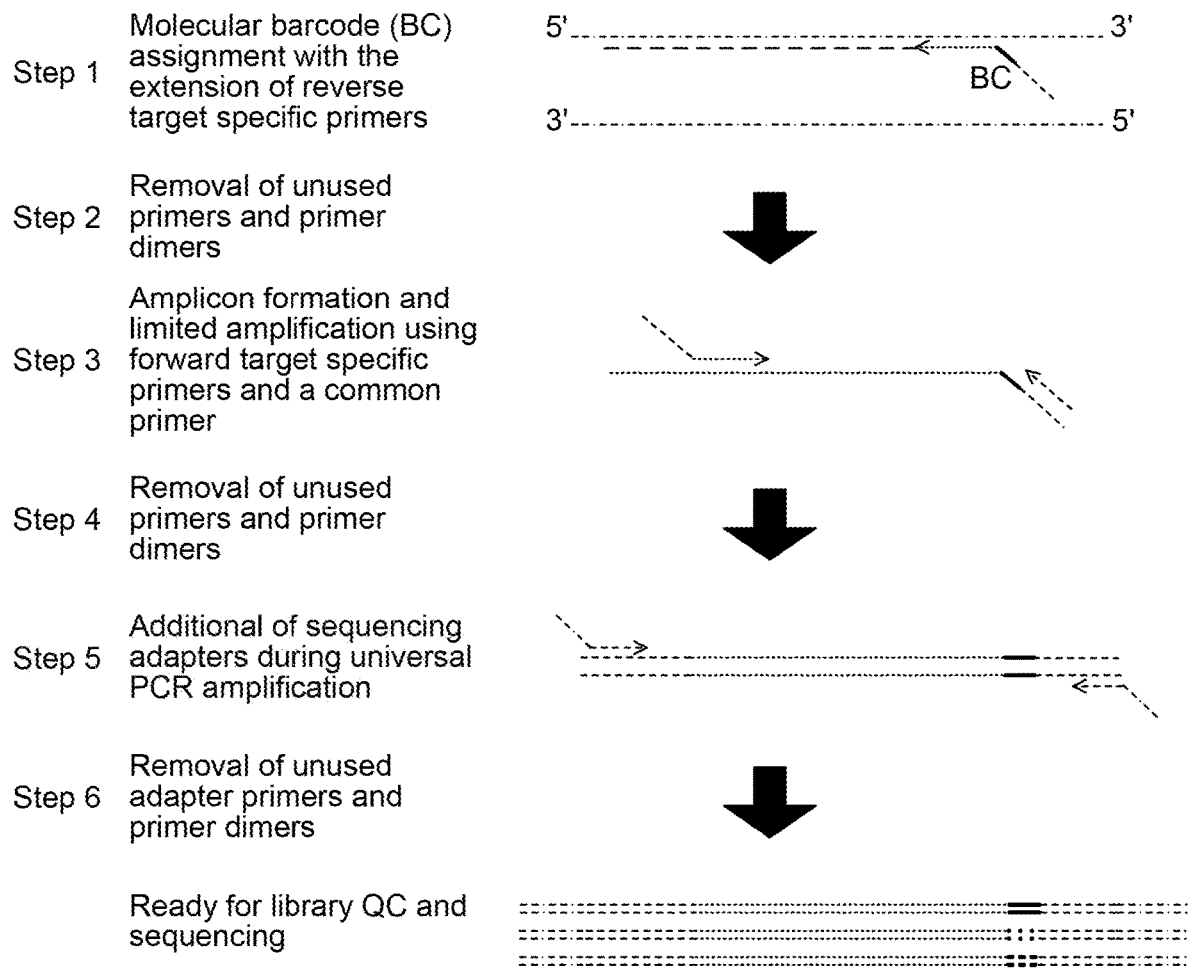
FIG. 7 shows an overview of an exemplary method for high multiplex PCR with molecular barcoding.

A schematic representation of the above method is shown in FIG. 7.

In another aspect, the present disclosure also provides kits for performing the methods described herein. The kits comprise the plurality of BC primers and the plurality of LA primers as described above in separate containers.

The kits may further comprise one or more of the following components:

(a) a primer comprising the $1^{st}$ universal primer sequence (US1), (b) a pair of universal primers for performing universal PCR (e.g., a pair of universal adapter primers) as described above, (c) one or more DNA polymerases as described above, and (d) one or more PCR reaction buffers.

PCR reaction buffers are known in the art. They typically include a monovalent cation (e.g., K$^+$), a buffering substance to maintain pH (e.g., Tris-HCl), and a divalent cation (e.g., Mg$^{2+}$ and Mn$^{2+}$). Additional components that may be included in PCR reaction mixtures include, for example, one or more of the following components: dimethyl sulfoxide (DMSO), bovine serum albumin (BSA), glycerol, formamide, dimethysulfoxide, tetramethylammonium chloride, potassium glutamate, ammonium sulfate, nonionic detergents, and cationic detergents.

In a related aspect, the present disclosure also provides use of the kits provided herein for preparing barcoded template nucleic acids or barcoded sequencing libraries and optional downstream sequencing analysis.

The methods and kits provided herein are useful in many applications where NGS is used, including targeted re-sequencing (e.g., targeted re-sequencing of tumors), genetic pathogen diversity analysis, and trascriptome profiling. In addition, NGS has been used in a variety of fields including metagenomics, paleogenomics, forensics, and human genetics to analyze subpopulations in complex biological samples. Clinical applications include prenatal screening for fetal aneuploidy, early detection of cancer, monitoring patients' response to therapy, and predicting treatment efficacy in individual patients.

The following examples are for illustration, and are not limiting.

EXAMPLES

Example 1

Detecting SNVs at Very Low Allelic Frequencies

Preparation of In Vitro "Genome in a Bottle" Sample Mixtures

Human genomic DNA samples of NA12878 and NA19129 were purchased from Coriell Institute. Sample mixture was created based on the actual amplifiable DNA in each sample, resulting in 2% of NA12878 DNA mixed in the NA19129 DNA. The resulting DNA mixture contains NA12878 variants present at 1-2% fraction. Homozygous SNVs unique for NA12878 are at 2% in the mixture, while heterozygous SNVs are at 1%. Most of the 134 variants from NA12878 are heterozygous SNVs.

380 Amplicon Panel Description

Primers were generated to target approximately 39 kb region in human genome. Primer pairs were selected based on optimal primer Tm, GC content, uniqueness of the primer sequence in human genome, low probability to form primer dimer and self-dimer, and collectively the ability to cover as many target regions as possible. Half of the primers were designed to cover 134 high-confidence SNVs from NA12878. The other half were designed to cover the protein coding regions of three genes: APC, SMAD4 and CTNNB1. To minimize primer dimer in high multiplex PCR, each 3' target specific sequence was selected to minimize potential cross hybridization with other primers. Specifically, a 3' target sequence would be redesigned when more than 10 bases at its 3' end would form perfect complementary match with another primer. All primers were synthesized by IDT (Coralville, Iowa).

380 Amplicon Panel Enrichment Protocol

DNA library was prepared according to the workflow described in FIG. 7. In brief, 10 to 80 ng DNA was used in each 10 ul reaction, together with 20 nM each BC primer, KOD DNA polymerase and reaction buffer (Toyobo, Japan). The following barcode assignment condition was used: 98° C. for 2 min, 55° C. for 15 min, 65° C. for 15 min, and 72° C. for 7 min. To ensure complete removal of excess BC primers, each sample was purified two rounds using GeneRead Size Selection Kit (QIAGEN, Germany). The purified DNA was then mixed in 25 ul with 20 nM each LA primer, 4 mM Mg$^{2+}$, 0.45 mM dNTP, 6U HotStarTaq and 1× miScript preamp buffer (QIAGEN, Germany). The reaction was done at following conditions: 95° C. for 15 min; one or three cycles of 95° C. for 15 seconds, 55° C. for 15 min and 65° C. for 15 min; 98° C. for 15 min. After that, universal adapter primers, new HotStarTaq and buffers were added in proportion to bring the reaction volume to 50 ul. The reaction was further incubated at the following conditions: 95° C. for 15 min; 23 cycles of 95° C. for 15 seconds and 60° C. for 2 min. Resulting DNA libraries were purified using GeneRead Size Selection Kit and quantified using GeneRead DNAseq Quantification Kit (QIAGEN, Germany). MiSeq sequencing was done following manufacturer's user manual (Illumina, CA).

The sequencing reads were processed as described below. Molecular barcodes were extracted from the raw reads using cutadapt tool. The universal sequences at the 5' end of the reads and the possible reverse complements of these sequences at the 3' ends of the reads were removed using two separate runs of cutadapt. The trimmed reads were then mapped to the genome using BWA. The molecular barcodes were extracted from trimmed reads by using the intended primer locations as reference points and extracting the bases between the 5' end of the trimmed read and the primer start position in the aligned read.

Next, to allow for the possibility of PCR or sequencing error within the barcode regions, a custom barcode clustering procedure was implemented to identify all barcodes that originated from the same initial molecular tag. The unique barcodes in each amplicon were ordered according to the number of reads containing the barcode. The clustering procedure assumed that an error-free barcode was present in many more reads than any single erroneous version of the barcode. Given this assumption, barcodes that were within edit distance of 1 from each other were clustered as long as one of them had at least 6× as many reads as the other. Some exceptions were made for barcodes with a single reads and barcodes that were not of the expected length, allowing for more aggressive clustering of these barcodes with other barcodes.

A consensus read was generated for all the reads in each cluster based on the alignments of these reads to the reference genome. At each position in the reference genome, both the abundance and base quality scores were used to pick the consensus base and assign a base quality. Then variant calling was performed on consensus reads using a standard pipeline consisting of BWA, GATK indel realigner, GATK base quality score recalibrator, GATK base alignment quality computation, primer trimming and MuTect.

It is usually very challenging to distinguish true SNVs present in the sample at very low fractions from sequencing artefacts, which also tend to be present at very low levels in the reads. This example demonstrates the benefit of molecular barcodes in removing these sequencing artefacts in detecting SNVs at very low fractions according to an exemplary method disclosed herein (see FIG. 7).

A sample containing a set of "known" SNVs at 1-2% fractions, by mixing DNAs of two well-defined individuals (NA12878 and NA19129) from the 1,000 Genomes Project as described above. A high-confidence variant set has been developed for NA12878 by NIST-led "Genome in a Bottle" Consortium (see Zook et al., Nat Biotechnol 32:246-51, 2014). Variant data are also available for NA19129 from the 1,000 Genome Project.

A total of 380 primer pairs were designed as described above. This 380-amplicon panel covered 39,231 bp region in the human genome, including 134 high confident SNVs that were heterozygous or homozygous non-reference in NA12878 and homozygous reference in NA19129. With this 380-amplicon panel, target enrichment using 10-80 ng genomic DNA mixtures was performed, following the high multiplex amplicon barcoding protocol as described above. After MiSeq sequencing, 4.1 to 5.2 million reads were generated from each sample with a mean coverage depth of at least 8300× (Table 1).

Reads from the same amplicon with the same molecular barcode were processed into one consensus read. All consensus reads were aligned to the reference genome and SNVs were identified. For 10, 20, 40 and 80 ng genomic DNA inputs, the mean coverage depths calculated using consensus reads were 98×, 187×, 336× and 530× respectively (Table 1).

TABLE 1

Summary of the sequencing runs for 380 amplicon panel

| | Input amount | | | | | |
|---|---|---|---|---|---|---|
| | 10 ng | 20 ng | 40 ng | 80 ng | 10 ng | 80 ng |
| LA cycles | 1 | 1 | 1 | 1 | 3 | 3 |
| Total reads | 5,161,694 | 5,029,394 | 4,181,410 | 4,568,978 | 4,612,940 | 8,718,690 |
| On-target reads | 4,449,285 | 4,226,778 | 3,528,081 | 4,051,939 | 3,591,578 | 7,704,936 |
| On-target read pairs | 2,152,647 | 2,066,226 | 1,707,379 | 1,972,168 | 1,715,098 | 3,659,067 |
| Median raw read depth | 9,263 | 8,558 | 6,454 | 6,915 | 7,701 | 16,275 |
| Mean raw read depth | 10,514 | 10,096 | 8,332 | 9,628 | 8,271 | 17,635 |
| % Base >0.2x mean | 95 | 94 | 92 | 90 | 95 | 96 |
| Median consensus read depth | 98 | 195 | 346 | 544 | 209 | 889 |
| Mean consensus read depth | 98 | 187 | 336 | 530 | 208 | 839 |
| Mean raw read/ consensus read | 53 | 28 | 13 | 11 | 22 | 16 |
| Median raw read/ consensus read | 53 | 26 | 11 | 8 | 20 | 10 |

TABLE 1-continued

Summary of the sequencing runs for 380 amplicon panel

| | Input amount | | | | | |
|---|---|---|---|---|---|---|
| | 10 ng | 20 ng | 40 ng | 80 ng | 10 ng | 80 ng |
| Bases in target region | 39,231 | 39,231 | 39,231 | 39,231 | 39,231 | 39,231 |
| GIAB high confident region for NA12878 | 29,343 | 29,343 | 29,343 | 29,343 | 29,343 | 29,343 |
| NA12878 unique SNVs | 134 | 134 | 134 | 134 | 134 | 134 |
| Detected true positives | 17 | 40 | 76 | 93 | 39 | 114 |
| Detected false positives | 0 | 2 | 3 | 5 | 4 | 3 |

Figure 8A:
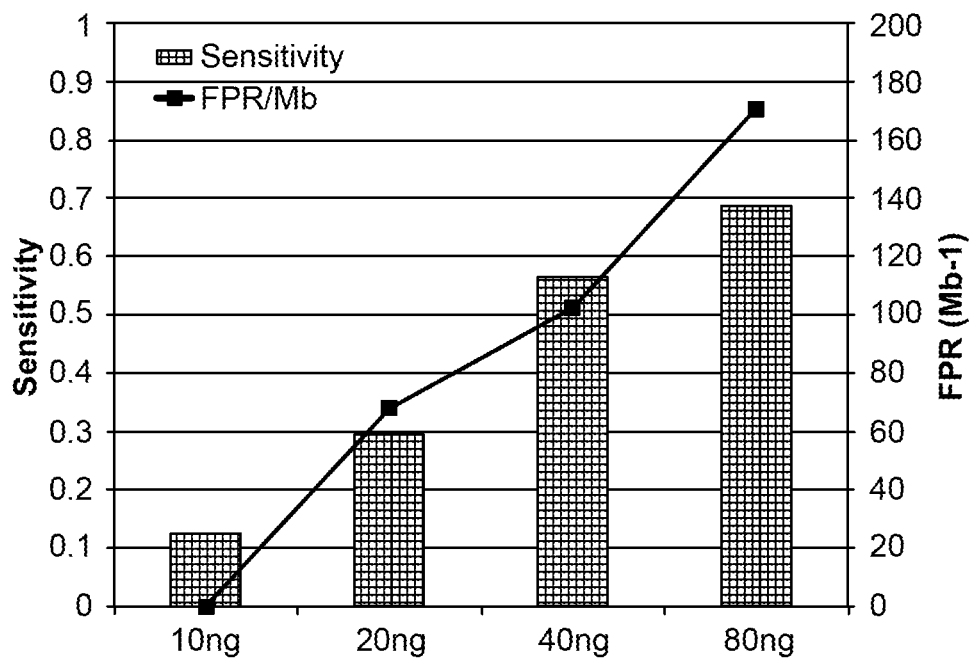
FIGS. 8A and 8B show comparison of sensitivity and false-positive rates (FPR) for different input DNA amounts. The x-axis represents different inputs of DNA admixtures. The left y-axis represents detection sensitivity for SNVs at 1-2% fraction. The right y-axis represents false positive rates. The sensitivity of SNV detection using the original protocol (i.e., performing only 1 cycle of limited amplification) (FIG. 8A) was improved after adding 3 cycles of limited amplification (FIG. 8B).

The number of consensus reads for a chromosomal locus is a reflection of the number of original DNA molecules being enriched for that locus. The higher number of coverage depth based on consensus reads reflected the more genomic DNA copies in the input samples. For SNV detection, 17 out of 134 (expected allelic frequency of 1-2%) high confident SNVs were detected (12.7% sensitivity) in 10 ng sample, with no false positives. The sensitivity increased as sample input increased, and could reach 68.9% with 5 false positive when 80 ng genomic DNA was used (FIG. 8A).

Figure 8B:
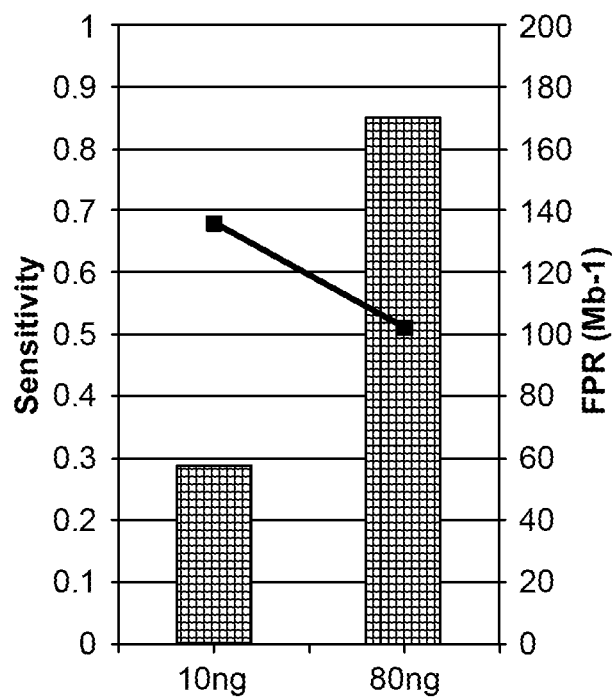

These initial results suggested that the more initial DNA molecules being converted to full amplicons by primer pairs, the better detection sensitivity could be achieved. To improve the sensitivity, approaches to improving the efficiency in forming full amplicons were investigated. One simple way was to do multiple cycles of LA primer annealing/extension, trying to convert as many barcoded DNA as possible into full amplicons. After Step 3 in the protocol was changed from 1 cycle to 3 cycles for 10 ng and 80 ng DNA inputs, the mean coverage depths for consensus reads increased from 98× to 208× and from 530× to 839× respectively (Table 1). As we expected, the sensitivity increased to 29.1% with 4 false positives, and to 85.1% with 3 false positives, respectively (FIG. 8b).

Example 2

Preparing Sequencing Library with Low Amount of Genomic DNA

934 Amplicon Panel Description

Additional 554 amplicons were designed using the same primer design algorithm as the 380 amplicon panel of Example 1, to cover all protein coding regions of another 12 genes: KRAS, TP53, AKT1, ATM, BRAF, FBXW7, PIK3CA, EGFR, ALK, NRAS, BAX and TGFBR2. Those primers were combined with the primers from 380-amplicon panel, resulting in the 934-amplicon panel. The combined panel covers a target region of approximately 87 kb.

934 Amplicon Panel Enrichment Protocol 1 ng human genomic DNA was mixed with 20 nM each BC primer, KOD DNA polymerase and reaction buffer (Toyobo, Japan). The following barcode assignment conditions were used: 98° C. for 2 min, 55° C. for 15 min, 65° C. for 15 min, and 72° C. for 7 min. To ensure complete removal of excess BC primers, each sample was purified two rounds using GeneRead Size Selection Kit. The purified DNA was then mixed in 25 ul with 20 nM each LA primer, 600 nM RS2 primer (which contains universal primer sequence of BC primers), 4 mM $Mg^{2+}$, 0.45 mM dNTP, 0.24U HotStarTaq and 1× miScript buffer. The reaction was continued according to the following conditions: 95° C. for 15 min; two cycles of 95° C. for 15 seconds and 60° C. for 15 min; eight cycles of 95° C. for 15 seconds and 60° C. 5 min. The PCR products were purified two round using the GeneRead Size Selection Kit. The purified DNA were further amplified in 25 ul using 400 nM universal adapter primers, 4 mM $Mg^{2+}$, 0.45 mM dNTP, 0.24U HotStarTaq and 1× miScript buffer, according to the following conditions: 95° C. for 15 min; 25 cycles of 95° C. for 15 seconds and 60° C. for 2 min. The amplification products were purified using GeneRead Size Selection Kit. The purified amplification products were 1:100 diluted. 10 ul of the diluted DNA was mixed with 1.25 ul NEBNext universal primer, 1.25 ul NEBNext index primers, and 12.5 ul 2×PCR buffer. The reaction was performed according to the following conditions: 95° C. for 30 seconds; 10 cycles of 98° C. for 10 seconds, 65° C. for 30 seconds, and 72° C. for 30 seconds; and 72° C. for 5 minutes. The resulting DNA libraries were purified using GeneRead Size Selection Kit, and quantified using GeneRead DNAseq Quantification Kit.

Figure 9:
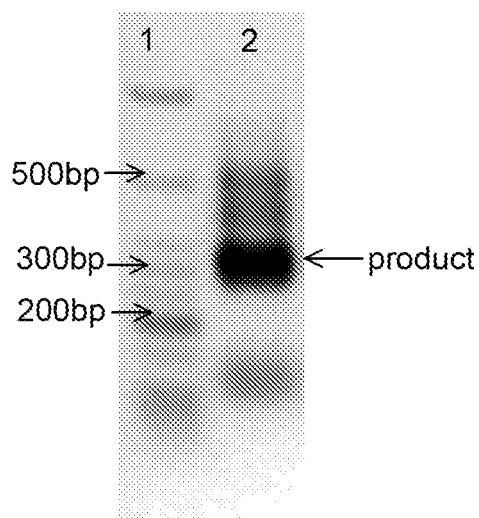
FIG. 9 shows electrophoresis of a sequencing library prepared as described in Example 2 (Lane 2). Lane 1: low molecular weight DNA ladder.

In this example, multiplex PCR was used to target 87 kb region in human genome using a panel of 930 pairs of primers. A quality library ready for sequencing was produced using as low as 1 ng genomic DNA (see FIG. 9).

Example 3

Measuring Low Abundant RNA Transcripts

ERCC RNA Amplicon Enrichment Protocol

ERCC RNA Spike-in Control Mix 1 was purchased from Life Technologies (Carlsbad, Calif.). It was further diluted 1:100 in the background of human normal universal RNA (BioChain, CA). 10 ng total RNA containing the ERCC RNA were reverse transcribed into cDNA using QuantiTect Reverse Transcription kit (QIAGEN, Germany). One fifth of the cDNA was used in the barcode assignment step together with 2 nM each BC primer, 16 mM $Mg^{2+}$, 6U HotStarTaq and 1× miScript preamp buffer. The following barcode assignment conditions were used: 95° C. for 15 min, 55° C. for 15 min, 65° C. for 15 min, and 72° C. for 7 min. To ensure complete removal of excess BC primers, reaction was purified in two rounds using GeneRead Size Selection Kit. The purified DNA was then mixed in 25 ul with 2 nM each non-BC primer, 4 mM $Mg^{2+}$, 0.45 mM dNTP, 6U HotStarTaq and 1× miScript preamp buffer. The reaction was continued at following conditions: 95° C. for 15 min; 20 cycles of 95° C. for 15 seconds and 55° C. for 5 min; 98° C. for 15 min. After that, universal adapter primers, new HotStarTaq and buffers were added in proportion to bring the reaction volume to 50 ul. The reaction was further incubated at the following conditions: 95° C. for 15 min; 26 cycles of 95° C. for 15 seconds and 60 C for 2 min. Resulting DNA libraries were purified using GeneRead Size Selection Kit, and quantified using GeneRead DNAseq Quantification Kit.

In this example, the use of high multiplex amplicon barcoding in targeted quantification of RNA transcripts was evaluated. To set up this experiment, ERCC RNA spike-in control mix was used as the sample, because each mix contains a defined number of copies for each RNA transcript (see External RNA Controls Consortium, BMC Genomics 6:150, 2005). The concentrations of 92 polyadenylated transcripts in the mix span $10^6$ fold concentration range. Based on the sequencing capacity of MiSeq, 25 transcripts were excluded with the highest concentrations from analysis, and 96 amplicons were designed for the rest 67 transcripts. For some of the longer transcripts, two amplicons were designed, one close to 5'end and the other close to 3'end. Following the high multiplex amplicon barcoding PCR and MiSeq sequencing, the abundance of RNA transcripts represented by each amplicon were measured by sequence reads and by counting unique molecular barcodes. They were compared to the expected amounts in the ERCC RNA mix. The variability in the first barcode assignment step and in the universal PCR amplification step was also examined.

Figure 10A:
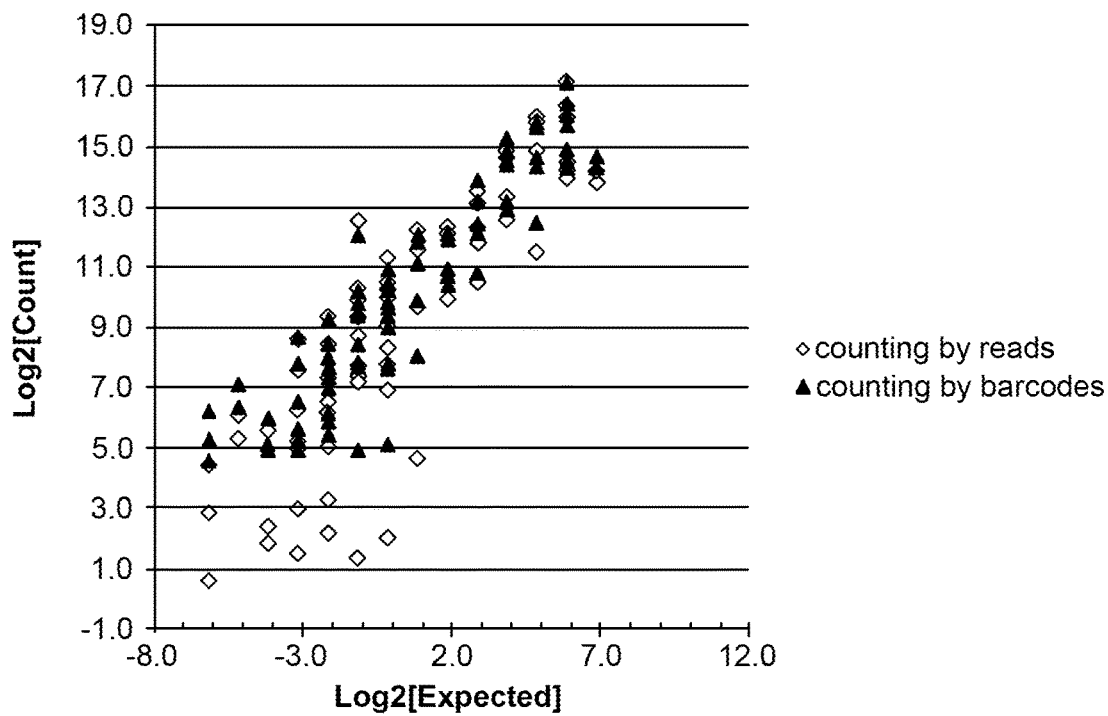
FIGS. 10A and 10B show ERCC RNA quantification using amplicon barcoding.

The measured transcript abundance by each amplicon overall correlated well with the expected levels (FIG. 10A). The correlations of the "measured" vs. the "expected" calculated by reads and barcodes were largely similar for higher abundant transcripts. However, for lower abundant transcripts, the correlation for measurements by barcodes was much better than those by reads as evidenced by more scattering of read data in the lower left corner. This suggests that the value of using molecular barcodes is more evident for quantifying targets of low abundance.

Figure 10B:
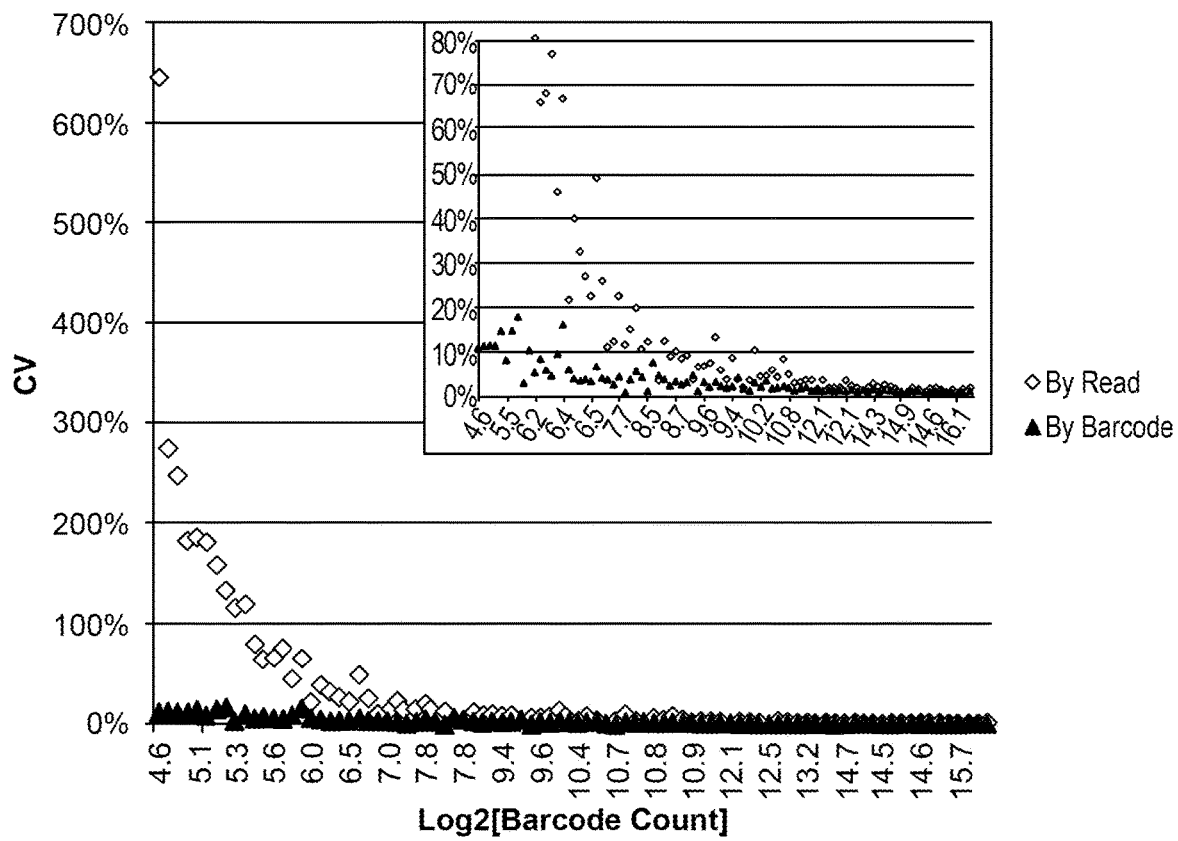

The technical reproducibility of the barcode assignment step was excellent (FIG. 10B). In addition, measurements using barcodes had much smaller technical noises when compared to those using sequence reads. Especially for those very low abundant transcripts, CV for barcodes was less than 10-20%, while CV for reads could be as high as 600%. Most of the technical noises observed in reads were results of universal PCR amplification, showing that PCR amplification can be highly stochastic and non-uniform, and counting molecular barcodes instead of reads can efficiently remove those PCR amplification noises.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for amplifying target nucleic acids in a nucleic acid sample, comprising:
   (a) extending each of a plurality of barcode primers (BC primers) to obtain extension products using the target nucleic acids as templates, wherein
      (i) each barcode primer comprises, from 5' to 3', a $1^{st}$ universal primer sequence (US1), a molecular tag sequence (MT), and a $1^{st}$ target-specific sequence (TS1),
      (ii) a plurality of barcode primers comprise at least 20 different barcode primers, and
      (iii) among the plurality of barcode primers (BC primers), the $1^{st}$ universal primer sequences (US1) are the same, but the $1^{st}$ target-specific sequences (TS1) are different,
      wherein step (a) is limited to a single cycle;
   (b) separating the plurality of barcode primers that have not been extended in step (a) from the extension products by size selection purification; and
   (c) amplifying the extension products of step (b) in the presence of a plurality of limited amplification primers (LA primers) to obtain a plurality of $1^{st}$ amplification products, wherein
      (i) each limited amplification primer comprises, from 5' to 3', a $2^{nd}$ universal primer sequence (US2) and a $2^{nd}$ target-specific sequence (TS2), and
      (ii) among the plurality of limited amplification primers, the $2^{nd}$ universal primer sequences (US2) are the same, but the $2^{nd}$ target-specific sequences (TS2) are different.

2. The method of claim 1, further comprising:
   (d) separating the plurality of unused limited amplification primers (LA primers) that have not been extended in step (c) from the 1st amplification products.

3. The method of claim 2, further comprising:
   (e) amplifying the $1^{st}$ amplification products in the presence of a pair of universal primers to obtain $2^{nd}$ amplification products, wherein one of the universal primers comprises at its 3'-terminus the $1^{st}$ universal primer sequence (US1), and the other of the universal primers comprises at its 3'-terminus the 2nd universal primer sequence (US2).

4. The method of claim 3, wherein each of the first and second universal primer sequences comprises an adapter sequence.

5. The method of claim 4, further comprising:
   (f) sequencing the $2^{nd}$ amplification products.

6. The method of claim 1, further comprising:
   (g) determining the copy number of one or more target nucleic acids.

7. The method of claim 1, further comprising:
   (h) identifying one or more genetic variations of interest in one or more target nucleic acids.

8. The method of claim 1, wherein each of the $1^{st}$ target-specific sequences of the plurality of barcode primers (BC primers) and the $2^{nd}$ target-specific sequences of the plurality of limited amplification primers (LA primers) does not contain more than 10 nucleotides that are complementary to any other barcode primers (BC primers) or to any other limited amplification primers (LA primers).

9. The method of claim 1, wherein when two of the target nucleic acids overlap with each other in genomic DNA, the TS1 sequences in the BC primers for the two target nucleic acids anneal to different strands of the genomic DNA.

10. The method of claim 1, wherein the molecular tag sequences (MT) in the plurality of barcode primers are completely or semi-defined.

11. The method of claim 1, wherein the molecular tag sequences (MT) in the plurality of barcode primers are completely random.

12. The method of claim 1, wherein the molecular tag sequences (MT) in the plurality of barcode primers are 5 to 15 nucleotides in length.

13. The method of claim 1, wherein the plurality of barcode primers (BC primers) comprises at least 500 different barcode primers, and the plurality of limited amplification primers (LA primers) comprises at least 500 different limited amplification primers.

14. The method of claim 1, wherein the number of different barcode primers (BC primers) of step (a) is the same as the number of the different limited amplification primers (LA primers) of step (c).

15. The method of claim 1, wherein the number of different barcode primers (BC primers) of step (a) is different from the number of the different limited amplification primer (LA primers) of step (c).

16. The method of claim 1, wherein step (a) is performed in the presence of a DNA polymerase that does not have strand displacement activity, flap endonuclease or 5'→3' exonuclease activity.

17. The method of claim 16, wherein the DNA polymerase is KOD DNA polymerase.

18. The method of claim 1, wherein step (c) is performed in the presence of another primer comprising the $1^{st}$ universal primer sequence.

19. The method of claim 18, wherein step (c) is performed by 2 to 16 cycles of polymerase chain reaction (PCR).

20. The method of claim 3, wherein either one or both of the universal primers comprise an index sequence (IDX) located 5' to the $1^{st}$ universal primer sequence (US1) or the $2^{nd}$ universal primer sequence (US2).

21. The method of claim 1, wherein the target nucleic acids are cDNA molecules.

22. The method of claim 1, wherein the target nucleic acids are microbial DNA molecules or mitochondrial DNA molecules.

23. The method of claim 1, wherein the target nucleic acids are genomic DNA molecules.

24. The method of claim 1 wherein the target nucleic acids are purified from a formalin-fixed, paraffin-embedded (FFPE) sample.

25. The method of claim 5, wherein the target nucleic acids are genomic DNA, and wherein step (f) determines the sequence of an at least 40 kb region of the genomic DNA.

26. The method of claim 25, wherein the genomic DNA is human genomic DNA, and the total amount of human genomic DNA used in step (a) is about 0.1 ng to about 1 µg.

27. The method of claim 6, wherein at least one target nucleic acid is of low abundance in the nucleic acid sample.

28. The method of claim 6, wherein its coefficient of variation (CV) of the copy number determination of substantially all of the one or more target nucleic acids is less than 20%.

29. The method of claim 7, wherein at least one genetic variation of interest has an allelic frequency of 5% or less in the nucleic acid sample.

30. The method of claim 7, having one or both of the following features:
   the sensitivity of step (h) is at least about 60%, and
   the specificity of step (h) is at least about 60%.

* * * * *

SEQUENCE LISTING

```
<160> NUMBER OF SEQ ID NOS: 8

<210> SEQ ID NO 1
<211> LENGTH: 48
<212> TYPE: DNA
<213> ORGANISM: Artificial Sequence
<220> FEATURE:
<223> OTHER INFORMATION: Exemplary BC primer
<220> FEATURE:
<221> NAME/KEY: misc_feature
<222> LOCATION: (1)...(48)
<223> OTHER INFORMATION: n = A,T,C or G

<400> SEQUENCE: 1
aatgtacagt attgcgtttt gnnnnnnnnn ncggcaggag acgaagag        48

<210> SEQ ID NO 2
<211> LENGTH: 21
<212> TYPE: DNA
<213> ORGANISM: Artificial Sequence
<220> FEATURE:
<223> OTHER INFORMATION: BC primer sequence

<400> SEQUENCE: 2
aatgtacagt attgcgtttt g                                     21
```

```
<210> SEQ ID NO 3
<211> LENGTH: 17
<212> TYPE: DNA
<213> ORGANISM: Artificial Sequence
<220> FEATURE:
<223> OTHER INFORMATION: BC primer sequence

<400> SEQUENCE: 3
cggcaggaga cgaagag                                                  17

<210> SEQ ID NO 4
<211> LENGTH: 38
<212> TYPE: DNA
<213> ORGANISM: Artificial Sequence
<220> FEATURE:
<223> OTHER INFORMATION: Exemplary LA primer

<400> SEQUENCE: 4
ttcttagcgt attggagtcc aaagccgagg aagctttg                           38

<210> SEQ ID NO 5
<211> LENGTH: 20
<212> TYPE: DNA
<213> ORGANISM: Artificial Sequence
<220> FEATURE:
<223> OTHER INFORMATION: LA primer sequence

<400> SEQUENCE: 5
ttcttagcgt attggagtcc                                               20

<210> SEQ ID NO 6
<211> LENGTH: 18
<212> TYPE: DNA
<213> ORGANISM: Artificial Sequence
<220> FEATURE:
<223> OTHER INFORMATION: LA primer sequence

<400> SEQUENCE: 6
aaagccgagg aagctttg                                                 18

<210> SEQ ID NO 7
<211> LENGTH: 79
<212> TYPE: DNA
<213> ORGANISM: Artificial Sequence
<220> FEATURE:
<223> OTHER INFORMATION: Universal adapter primers, Uni.Primer1

<400> SEQUENCE: 7
aatgatacgg cgaccaccga gatctacact ctttccctac acgacgctct tccgatctaa   60
tgtacagtat tgcgttttg                                                79

<210> SEQ ID NO 8
<211> LENGTH: 84
<212> TYPE: DNA
<213> ORGANISM: Artificial Sequence
<220> FEATURE:
<223> OTHER INFORMATION: Universal adapter primers, Uni.Primer2

<400> SEQUENCE: 8
caagcagaag acggcatacg agatacatcg gtgactggag ttcagacgtg tgctcttccg   60
atctttctta gcgtattgga gtcc                                          84
```